(12) United States Patent  
Schroeder et al.

(10) Patent No.: US 7,711,084 B2
(45) Date of Patent: *May 4, 2010

(54) PROCESSES AND A DEVICE FOR DETERMINING THE ACTUAL POSITION OF A STRUCTURE OF AN OBJECT TO BE EXAMINED

(75) Inventors: Mario Schroeder, Puttlingen (DE); Wolfram Schmidt, Saarbrucken (DE)

(73) Assignee: MYCRONA Gesellschaft fur innovative Messtechnik GmbH, Saarwellingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/157,103

(22) Filed: Jun. 6, 2008

(65) Prior Publication Data

US 2008/0285710 A1  Nov. 20, 2008

Related U.S. Application Data

(62) Division of application No. 10/616,606, filed on Jul. 10, 2003, now Pat. No. 7,386,090.

(30) Foreign Application Priority Data

Jul. 12, 2002  (DE)  ................................ 102 31 896

(51) Int. Cl.
*A61B 6/03* (2006.01)

(52) U.S. Cl. ............................................. 378/20; 378/4
(58) Field of Classification Search ..................... 378/4, 378/8, 15, 19, 20, 205, 901; 600/415, 417, 600/429

See application file for complete search history.

(56) References Cited

U.S. PATENT DOCUMENTS 5,682,414 A * 10/1997 Saito .......................... 378/901
6,490,477 B1 * 12/2002 Zylka et al. .................. 600/429
7,386,090 B2 * 6/2008 Schroeder et al. ............. 378/20

* cited by examiner

*Primary Examiner*—Chih-Cheng G Kao
(74) *Attorney, Agent, or Firm*—Horst M. Kasper

(57) ABSTRACT

A CT scanner is employed having a first coordinate system called the CT coordinate system related to the CT scanner for determining an actual position of a structure of an object to be examined. A coordinate measuring instrument (MI) is employed which is either a tactile or an optical or multisensor or an ultrasonic coordinate measuring instrument and which has a second coordinate system, the MI coordinate system, related to said coordinate measuring instrument. According to a variant, a) the coordinates of the object are determined in the MI coordinate system, b) the target position of the structure is predefined, c) after steps a) and b) the target position is determined in the MI coordinate system, d) and, the object is positioned in such a way that the target position of the structure comes to lie within a volume detected by the CT scanner using the result of step c).

38 Claims, 1 Drawing Sheet

Figure 1:
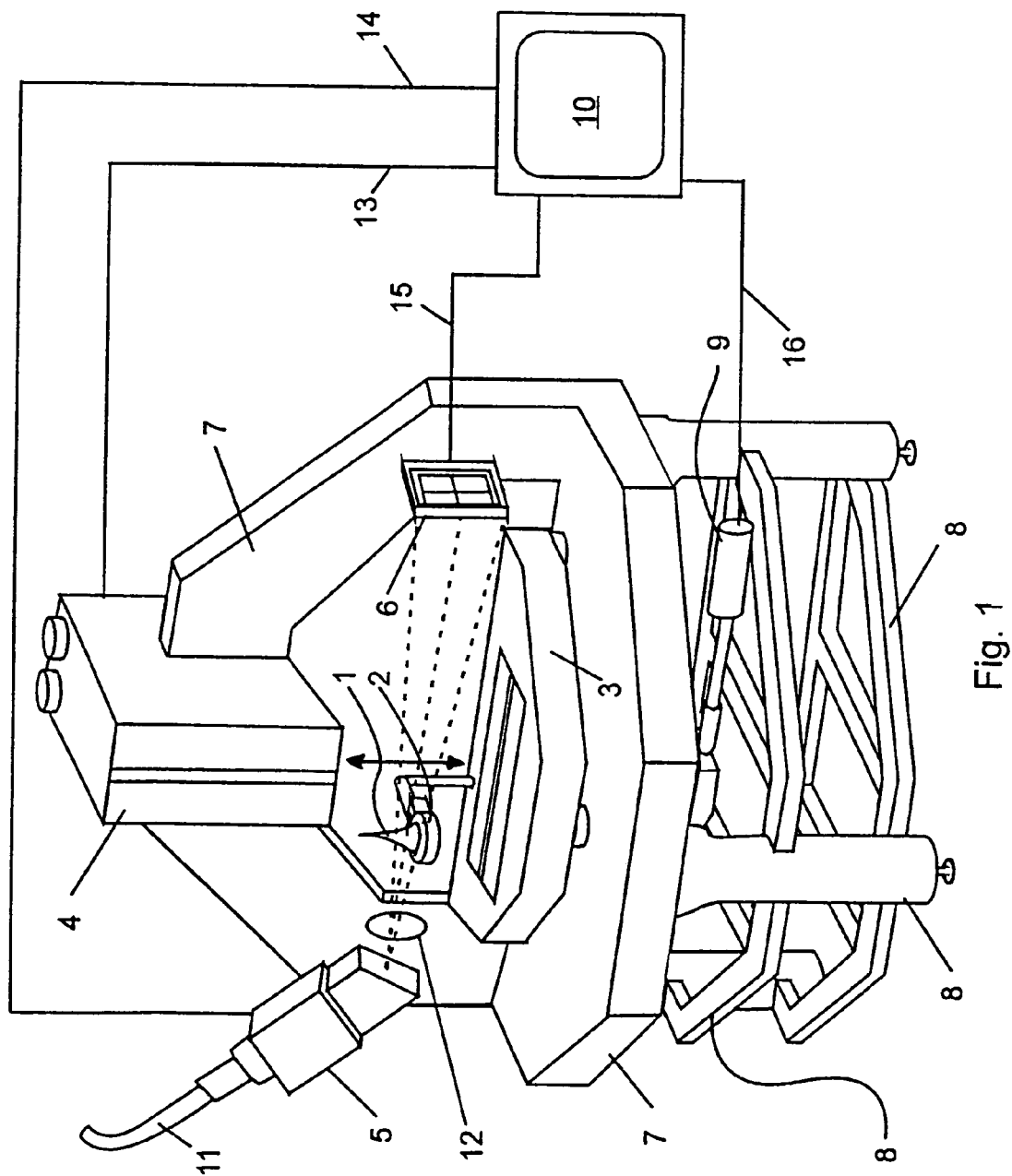

PROCESSES AND A DEVICE FOR DETERMINING THE ACTUAL POSITION OF A STRUCTURE OF AN OBJECT TO BE EXAMINED

CROSS-REFERENCE TO RELATED APPLICATIONS

This application is a divisional application of the patent application Ser. No. 10/616,606, filed on Jul. 10, 2003 and issued as U.S. Pat. No. 7,386,090 B2 on Jun. 10, 2008.

STATEMENT REGARDING FEDERALLY SPONSORED RESEARCH OR DEVELOPMENT (not applicable)

THE NAMES OF THE PARTIES TO A JOINT RESEARCH AGREEMENT (not applicable)

INCORPORATION-BY-REFERENCE OF MATERIAL SUBMITTED ON A COMPACT DISC (See 37 CFR 1.52(e)(5) and MPEP 608.05. Computer program listings (37 CFR 1.96(c)), "Sequence Listings" (37 CFR 1.821(c)), and tables having more than 50 pages of text are permitted to be submitted an compact discs.) or

REFERENCE TO A "MICROFICHE APPENDIX"

(See MPEP § 608.05(a), "Microfiche Appendices" were accepted by the Office until Mar. 1,2001.)
(not applicable)

BACKGROUND OF THE INVENTION (1) Field of the Invention

The invention relates to processes and to a device for determining the actual position of a structure of an object to be examined in a coordinate system.

(2) Description of Related Art including information disclosed under 37 CFR 1.97 and 1.98

Computed tomography scanners serve to create three-dimensional images, namely, so-called CT scans, of objects such as, for example, workpieces or human bodies or body parts, whereby these images also show internal structures of the object.

In computed tomography technology, abbreviated as CT technology, X-rays are used to take images of an object or of a part thereof from many different directions, that is to say, the object is X-rayed sequentially from many different directions. Thus, a computed tomography scanner, hereinafter referred to as a CT scanner, has an X-ray source and a two-dimensional position-resolving detector, for example, a CCD matrix, that is sensitive to the radiation emitted by the X-ray source. The X-ray source emits radiation, typically, for instance, of 450 keV. The object is positioned between the X-ray source and the detector and it is rotated incrementally with respect to the X-ray source or to the screen, or conversely, the CT scanner is rotated incrementally around the object, which in this case remains stationary.

When it is not the CT scanner but rather the object that is rotated, the CT scanner generally has an object support stage on which the object is placed. The object support stage can travel in such a way that the object can be positioned in the beam path of the X-rays. Moreover, the object support stage is rotatable so that the object can be rotated in order to create the CT image. Typically, the object is rotated, for example, in increments of 0.9° each, so that 400 rotation steps amount to a full revolution of the object. In this manner, the CT scanner can detect a certain volume that comprises either the entire object or a part thereof.

For each of the rotational positions that the object passes through, the detector takes a two-dimensional transmission X-ray image of the object. On these two-dimensional images, the object appears larger than it is in reality since its size on the image corresponds to a centered projection of the object on the detector surface, whereby the X-ray source is the center of projection.

Based on the array of two-dimensional individual images obtained in this manner, a computer is used to calculate a three-dimensional digital image of the volume detected by the CT scanner, i.e. of the object or of a part thereof, said image also showing internal structures that are completely enclosed in the object, insofar as these internal structures have an absorption coefficient for the radiated X-rays that differs from their surroundings, which is the case, for example, with cavities such as drilled holes.

After each full revolution of the object, the object support with the object can be shifted translatorily by a certain distance and the process explained above can be carried out again.

Such a commercially available CT scanner is described, for example, in the brochure: "RayScan 3D-X-Ray Computed Tomography", PRO-RS-A-E000 11/01, made by Hans Walischmiller GmbH, D-88677 Markdorf, Germany.

Such CT scanners can be used to examine the internal structures of objects, for example, drilled holes in workpieces. In order to examine a structure of the object in this manner, first of all, a CT image of the entire object, including the structure of interest, can be created.

A drawback here is that, as a rule, the image of the structure only occupies a small part of the image field of the CT scanner since the CT scanner can only achieve a limited relative spatial resolution. This is especially due to the finite diameter of the exit pupil of the X-ray source and to the limited number of pixels of the CCD matrix; typically, a relative lateral resolution of, for example, 1:4000 can be achieved.

Therefore, in this case, a structure of the object whose extension is, for example, 1% of the object size, is only imaged at a relative resolution of 1:40 which, in most cases, is insufficient for a detailed examination of the structure.

Therefore, the CT image of the object can be used to determine the location of the structure within the object with respect to the coordinate system of the CT scanner and to carry out a second CT scan of the object, while regulating the CT scanner in such a way that only the immediate vicinity of the structure is detected by the CT scanner and a second CT image of this vicinity is made with a greater magnification factor. In this manner, the relative resolution of the image of the structure is enhanced, that is to say, more details of the structure become visible.

However, this also entails disadvantages. For example, it is a demanding procedure to determine the location within the object on the basis of the first CT image. Moreover, such a localization of the structure is imprecise since not only the structure itself but also the surface of the object can only be detected with the limited resolution of the CT scanner, as a result of which the appertaining measuring uncertainties become greater.

Moreover, additional time is required to create the second CT image. In view of the very high operating costs of a CT scanner, this need for additional time is a substantial cost factor in examining the structure.

Furthermore, in order to create the second CT image, the object is once again exposed to a certain dose of ionizing radiation. This is especially disadvantageous or problematic if the object consists of living biological matter. The repeated radiation exposure can also have a detrimental effect on non-living material. Ionizing radiation can trigger, for example, ageing, transformation, discoloration or degradation of plastics, it can have an altering effect on crystal structures or it can destroy electronic modules.

BRIEF SUMMARY OF THE INVENTION

Therefore, the invention is based on the objective of creating a process and a device that allow a localization and examination of a structure of an object so as to be less time-consuming and to allow greater precision and reduced radiation exposure of the object.

This objective is achieved according to the invention by a process for determining the actual position of a structure of an object to be examined in a coordinate system, whereby a CT scanner is employed which uses CT technology, having a first coordinate system, the CT coordinate system, related to said CT scanner, and a coordinate measuring instrument (MI) is employed which is either a tactile or an optical coordinate measuring instrument or a multisensor coordinate measuring instrument or an ultrasonic coordinate measuring instrument, having a second coordinate system, the MI coordinate system, related to said coordinate measuring instrument, whereby
a) the coordinates of the object to be examined are determined in the MI coordinate system,
b) a target position of the structure within the object to be examined is predefined,
c) after the execution of steps a) and b), the target position is determined in the MI coordinate system,
d) and, using the result of step c), the object to be examined is positioned in such a way that the target position of the structure comes to lie within the volume detected by the CT scanner.

Furthermore, this objective is achieved by a process for determining the actual position of a structure of an object to be examined in a coordinate system, whereby a CT scanner is employed which uses CT technology, having a first coordinate system, the CT coordinate system, related to said CT scanner, and a coordinate measuring instrument is employed which is either a tactile or an optical coordinate measuring instrument or a multisensor coordinate measuring instrument or an ultrasonic coordinate measuring instrument, having a second coordinate system, the MI coordinate system, related to said coordinate measuring instrument, whereby
a) the coordinates of the object to be examined are determined in the CT coordinate system,
b) a target position of the structure within the object to be examined (1) is predefined,
c) after the execution of steps a) and b), the target position is determined in the CT coordinate system,
d) and, using the result of step c), the object to be examined is positioned in such a way that the target position of the structure comes to lie within the area that can be detected by the coordinate measuring instrument.

Moreover, the objective is achieved by a device for determining the actual position of a structure of an object to be examined in a coordinate system, with a CT scanner having a first coordinate system, the CT coordinate system, related to said CT scanner, and a coordinate measuring instrument is employed which is either a tactile or an optical coordinate measuring instrument or a multisensor coordinate measuring instrument or an ultrasonic coordinate measuring instrument, having a second coordinate system, the MI coordinate system, related to said coordinate measuring instrument, whereby the coordinates of the object to be examined can be determined in the MI coordinate system, and a target position of the structure within the object to be examined is predefined, so that the target position can be determined in the MI coordinate system, and the object to be examined can be positioned in such a way that the target position of the structure comes to lie within the volume detected by the CT scanner, whereby the CT scanner and the multisensor coordinate measuring instrument are integrated into one single device.

Therefore, the first coordinate system is the CT coordinate system that is related to the CT scanner. The second coordinate system is the MI coordinate system; the latter is related to the coordinate measuring instrument.

Therefore, in the process according to the invention for determining the actual position of a structure of an object to be examined in a coordinate system, a CT scanner is employed, having a first coordinate system, the CT coordinate system, related to said CT scanner, and a coordinate measuring instrument is employed which is either a tactile or an optical coordinate measuring instrument or a multisensor coordinate measuring instrument or an ultrasonic coordinate measuring instrument, having a second coordinate system, the MI coordinate system, related to said coordinate measuring instrument.

The device according to the invention for determining the actual position and the shape of a structure of an object to be examined in a coordinate system comprises a CT scanner, having a first coordinate system, the CT coordinate system, related to said CT scanner, and a coordinate measuring instrument which is either a tactile or an optical coordinate measuring instrument or a multisensor coordinate measuring instrument or an ultrasonic coordinate measuring instrument, having a second coordinate system, the MI coordinate system, related to said coordinate measuring instrument.

According to a variant of the process, in the case of a predefined target position of the structure, relative to at least three selected, non-co-linear points of the object to be examined, said object is positioned using the coordinate measuring instrument in such a way that at least a part of the object to be examined lies within the volume detected by the CT scanner and this part of the object to be examined contains the target position of the structure.

Therefore, according to an embodiment of the device according to the invention, in the case of a predefined target position of the structure, relative to at least three selected, non-co-linear points of the object to be examined, said object can be positioned using the coordinate measuring instrument in such a way that at least a part of the object to be examined lies within the volume detected by the CT scanner and this part of the object to be examined contains the target position of the structure.

The selected points can be located especially on the surface of the object to be examined. The selected points can be marked, for example, by means of color, in order to facilitate their detection in the MI coordinate system. Another possibility is to use, as the selected points, those points that are designated on the basis of the geometry or shape of the object to be examined such as, for example, the corner points.

In a variant of the process, at a predefined maximum deviation of the target position from the actual position of the structure of the object to be examined, said object is positioned using the coordinate measuring instrument in such a way that the target position as well as the actual position of the structure lie within the volume detected by the CT scanner.

Therefore, according to an embodiment of the device according to the invention, at a predefined maximum-deviation of the target position from the actual position of the structure of the object to be examined, said object can be positioned using the coordinate measuring instrument in such a way that the target position as well as the actual position of the structure lie within the volume detected by the CT scanner.

The actual position of the structure can deviate from the target position, for example, as a result of manufacturing tolerances. In actual practice, it is often possible to indicate the maximum anticipated or possible deviation of the actual position from the target position of the structure.

According to a variant of the process, the actual position differs from the target position by a predefined tolerance deviation at the most, so that the actual position lies within a tolerance volume whose edge is at a distance from the target position by the tolerance deviation at the most, whereby the object to be examined is positioned using the coordinate measuring instrument in such a way that the tolerance volume lies completely within the volume detected by the CT scanner.

In an embodiment of the device according to the invention, the actual position differs from the target position by a predefined tolerance deviation at the most, so that the actual position lies within a tolerance volume whose edge is at a distance from the target position by the tolerance deviation at the most, whereby the object to be examined can be positioned using the coordinate measuring instrument in such a way that the tolerance volume lies completely within the volume detected by the CT scanner.

In particular, the tolerance volume can be a sphere, a tolerance sphere, whose mid-point coincides with the target positions and whose radius is predefined by the magnitude of the maximum deviation of the target position from the actual position of the structure.

According to a variant of the process, the object to be examined is positioned using the coordinate measuring instrument in such a way that the volume detected by the CT scanner has, at the most, the x-fold volume of the tolerance sphere or of the tolerance volume, whereby x is a predefinable number that is preferably greater than 1.

In a variant of the device according to the invention, the object to be examined can be positioned using the coordinate measuring instrument in such a way that the volume detected by the CT scanner has, at the most, the x-fold volume of the tolerance sphere or of the tolerance volume, whereby x is a predefinable number that is preferably greater than 1.

For example, the object to be examined can be positioned using the coordinate measuring instrument in such a way that the volume detected by the CT scanner is, at the most, two times the volume of the tolerance sphere or of the tolerance volume, which means that the number x in this example equals 2.

According to another example, the object to be examined is positioned using the coordinate measuring instrument in such a way that the volume detected by the CT scanner is, at the most, four times the volume of the tolerance sphere or of the tolerance volume, which means that the number x in this example equals 4.

According to a variant,
in the case of a predefined target position of the structure, relative to at least three selected, non-co-linear points of the object to be examined (1), the object to be examined (1) is positioned using the CT scanner in such a way that
at least a part of the object to be examined (1) lies within the area that can be detected by the coordinate measuring instrument and this part of the object to be examined (1) contains the target position of the structure, at a predefined maximum deviation of the target position from the actual position of the structure of the object to be examined (1), said object is positioned using the CT scanner in such a way that the target position as well as the actual position of the structure lie within the area that can be detected by the coordinate measuring instrument, whereby the actual position differs from the target position by a predefined tolerance deviation at the most, so that the actual position lies within a tolerance area whose edge is at a distance from the target position by the tolerance deviation at the most, the object to be examined (1) is positioned using the CT scanner in such a way that the tolerance area lies completely within the area that can be detected by the coordinate measuring instrument.

The relative location and the relative orientation of the CT coordinate system relative to the MI coordinate system can be predefined or can be determined by means of calibration. Therefore, according to an embodiment, the relative location and the relative orientation of the CT coordinate system relative to the MI coordinate system are predefined or can be determined by means of calibration.

According to a variant, the following steps are carried out:
(i) by means of the coordinate measuring instrument, the location of the at least three selected points of the object to be examined (1) is determined relative to the MI coordinate system,
(ii) the target position of the structure relative to the MI coordinate system is calculated using the measured results obtained in step (i), and
(iii) the target position of the structure is converted from the MI coordinate system to the CT coordinate system so that subsequently the location of the target position in the CT coordinate system is known.

According to an embodiment,
(i) by means of the coordinate measuring instrument, the location of the at least three selected points of the object to be examined (1) can be determined relative to the MI coordinate system,
(ii) the target position of the structure relative to the MI coordinate system can be calculated using the measured results obtained in step (i), and
(iii) the target position of the structure can be converted from the MI coordinate system to the CT coordinate system so that the location of the target position can be determined in the CT coordinate system.

According to a variant, the object to be examined is positioned relative to the CT scanner by means of a traveling mechanism, using the target position of the structure obtained by means of step (iii) with respect to the CT coordinate system, in such a way that the tolerance volume and thus also the structure lie within the volume detected by the CT scanner.

Therefore, according to an embodiment of the invention, the object to be examined can be positioned relative to the CT scanner by means of a traveling mechanism, using the target position of the structure obtained by means of step (iii) with respect to the CT coordinate system, in such a way that the tolerance volume and thus also the structure lie within the volume detected by the CT scanner.

According to a variant, using the CT scanner, a three-dimensional digital CT image of the tolerance volume, including the structure, is created and stored as a CT data record, and the actual position of the structure is determined in the CT coordinate system on the basis of the CT data record.

Therefore, according to an embodiment, using the CT scanner, a three-dimensional digital CT image of the tolerance volume, including the structure, can be created and stored as a CT data record, and the actual position of the structure can be determined in the CT coordinate system on the basis of the CT data record.

According to a variant, (i) by means of the CT scanner, the location of the at least three selected points of the object to be examined is determined relative to the CT coordinate system, (ii) the target position of the structure relative to the CT coordinate system is calculated using the measured results obtained in step (i), (iii) the target position of the structure is converted from the CT coordinate system to the MI coordinate system so that subsequently the location of the target position in the CT coordinate system is known, (iv) the object to be examined is positioned relative to the coordinate measuring instrument by means of a traveling mechanism, using the target position of the structure obtained by means of step (iii) with respect to the MI coordinate system, in such a way that the tolerance volume and thus also the structure lie within the area that can be detected by the coordinate measuring instrument, (v) using the coordinate measuring instrument, a three-dimensional digital image of the tolerance area, including the structure, is created and stored as an MI data record, and the actual position of the structure is determined in the MI coordinate system on the basis of the MI data record.

According to a preferred variant of the process according to the invention, the CT scanner used is one that has an X-ray source and a two-dimensional, position-resolving detector having an active detector surface that is sensitive to the radiation emitted by the X-ray source, whereby the image field of the CT scanner is defined by the size of the active sensor or detector surface, the target position of the structure, relative to at least three selected, non-co-linear points of the object to be examined, is predefined and the actual position differs from the target position by a tolerance deviation at the most, so that the actual position lies within a, for example, spherical tolerance volume whose edge is at a distance from the target position by the tolerance deviation at the most. The relative location and the relative orientation of the CT coordinate system relative to the MI coordinate system here are either already known or else are determined by means of calibration.

The coordinate measuring instrument can be a tactile coordinate measuring instrument, that is to say, based on mechanical tracing, or an optical coordinate measuring instrument or, for instance, a laser-aided multisensor coordinate measuring instrument or an ultrasonic coordinate measuring instrument. Thus, the coordinate measuring instrument can particularly be one that is not capable of detecting internal structures of the object to be examined.

According to this variant, the following steps are carried out:

a) by means of the coordinate measuring instrument, the location of the at least three selected points of the object to be examined are determined relative to the MI coordinate system, b) the target position of the structure relative to the MI coordinate system is calculated using the measured results obtained in step a), c) the target position of the structure is converted from the MI coordinate system to the CT coordinate system, so that the location thereof in the CT coordinate system is known, d) the relative position of the object to be examined is regulated with respect to the CT scanner by means of a traveling mechanism, using the target position of the structure obtained by means of step c) relative to the CT coordinate system, in such a way that the tolerance volume and thus also the structure lie within the volume that can be detected by the CT scanner, e) by means of the CT scanner, a three-dimensional digital CT image of the tolerance volume, including the structure, is created and stored as a CT data record, and f) the actual position of the structure is determined in the CT coordinate system on the basis of the CT data record.

This means that the CT scanner, using the measurements carried out by the coordinate measuring instrument, the relative location and the relative orientation of the CT coordinate system and the MI coordinate system of the CT scanner can advantageously be regulated in such a way that, right from the start, the structure is located in the area of the object to be examined that is detected and imaged by the CT scanner.

According to a preferred embodiment of the device according to the invention, the CT scanner has an X-ray source and a two-dimensional position-resolving detector having an active detector surface that is sensitive to the radiation emitted by the X-ray source, whereby the image field of the CT scanner is defined by the size of the active detector surface, the target position of the structure, relative to at least three selected, non-co-linear points of the object to be examined, is predefined, and the actual position differs from the target position by a tolerance deviation at the most, so that the actual position lies within a, for example, spherical tolerance volume whose edge is at a distance from the target position by the tolerance deviation at the most, and the relative location and the relative orientation of the CT coordinate system relative to the MI coordinate system are known or can be determined by means of calibration, whereby a) by means of the coordinate measuring instrument, the location of the at least three selected points of the object to be examined can be determined relative to the MI coordinate system, b) the target position of the structure relative to the MI coordinate system can be calculated from this, c) the target position of the structure can be converted from the MI coordinate system to the CT coordinate system, so that the location thereof can be determined in the CT coordinate system, d) the relative position of the object to be examined relative to the CT scanner can be regulated by means of a traveling mechanism, using the target position of the structure relative to the CT coordinate system, in such a way that the tolerance volume and thus also the structure lie within the volume that can be detected by the CT scanner, and e) the CT scanner can create a three-dimensional digital CT image of the tolerance volume, including the structure, and can store it as a CT data record, so that the actual position as well as the shape of the structure can be determined in the CT coordinate system on the basis of the CT data record.

The term active detector surface refers to the surface of the detector that can be used to register the radiation from the X-ray source. The term image field of the CT scanner refers to the extension of the projection of the volume detected by the CT scanner on the plane of the detector surface.

Thus, according to the invention, the possibility is created to operate the computed tomography scanner, CT scanner for short, at such a high magnification that it can no longer synchronously image the entire object to be examined, and in doing so, regulate the relative position between the CT scanner and the object to be examined right from the start in such a manner that advantageously the tolerance volume and thus also the structure are always detected by the CT scanner.

In order to determine the target position of the structure relative to the MI coordinate system, the measurement of at least three selected points of the object to be examined relative to the MI coordinate system is required; if more than three points are measured in the above-mentioned manner, then the additional measured results can advantageously be used to decrease the mean error and thus to increase the achieved accuracy.

An advantage of the invention lies in the fact that the outer shape of workpieces or other objects, for example, in mass production, is already often routinely measured with a tactile or an optical coordinate measuring instrument or with a multisensor coordinate measuring instrument, for example, for purposes of production monitoring. In these cases, the results of step a) are available right from the start so that step a) does not involve any additional effort.

The tolerance volume can especially be rotation-symmetrical, i.e. a tolerance sphere, so that its radius is defined by the tolerance deviation and its mid-point is defined by the target position.

According to an advantageous variant of the invention, the CT scanner in process step d) is regulated in such a way that the center of the tolerance volume is essentially located in the center of the volume that can be detected by the CT scanner. Therefore, the CT scanner can preferably be regulated in such a way that the center of the tolerance volume is located essentially in the center of the volume that can be detected by the CT scanner.

This means that the CT scanner is regulated according to the invention in such a way that, right from the start, the target position of the structure is advantageously in the center of the area of the object to be examined that is detected and imaged by the CT scanner; the invention makes it possible to right away "center" the target position of the structure in the area that can be detected by the CT scanner.

According to a variant, the CT scanner is regulated in such a way that, with the centered projection of the tolerance volume with the X-ray source as the center of projection, the image field is completely filled by the projection of the tolerance volume onto the detector, so that the relative lateral resolving power of the active detector surface is fully utilized for detecting the tolerance volume. In this case, the CT scanner can be regulated in such a way that, with the centered projection of the tolerance volume with the X-ray source as the center of projection, the image field is completely filled by the projection of the tolerance volume onto the detector.

According to another preferred variant, the CT scanner is regulated in such a way that, with the centered projection of the tolerance volume with the X-ray source as the center of projection, the smallest diameter of the projection of the tolerance volume onto the detector and the smallest diameter of the image field of the CT scanner are essentially equal in size, or the largest diameter of the projection of the tolerance volume onto the detector and the largest diameter of the image field of the CT scanner are essentially equal in size.

According to another variant, the CT scanner is regulated in such a way that, with the centered projection of the tolerance volume with the X-ray source as the center of projection, the largest diameter of the projection of the tolerance volume onto the detector and the smallest diameter of the image field of the CT scanner are essentially equal in size.

In a variant, the CT scanner can be regulated in such a way that, with the centered projection of the tolerance volume with the X-ray source as the center of projection, the smallest diameter of the projection of the tolerance volume onto the detector and the smallest diameter of the image field of the CT scanner are essentially equal in size, or the largest diameter of the projection of the tolerance volume onto the detector and the largest diameter of the image field of the CT scanner are essentially equal in size.

According to another variant, the CT scanner can be regulated in such a way that, with the centered projection of the tolerance volume with the X-ray source as the center of projection, the largest diameter of the projection of the tolerance volume onto the detector and the smallest diameter of the image field of the CT scanner are essentially equal in size.

In this manner, the magnification factor used to create the CT image can be adapted to the dimensions of the image field and to the size of the tolerance volume in such a way that the projection of the tolerance volume essentially corresponds to the size of the image field. In this manner, the magnification factor can advantageously be selected in such a way that it is the largest possible factor at which the tolerance volume can still just barely be completely detected in its entirety by the CT scanner so that, right from the start, the structure is advantageously located in the area detected and imaged by the CT scanner. Therefore, even at a high magnification factor, there is no risk that the structure will lie outside of the area that can be detected by the CT scanner. Here, the relative lateral resolving power of the active detector surface is largely utilized for the detection of the tolerance volume.

The object to be examined can be, for example, a vehicle fuel-injection nozzle with a typical length of 50 mm and a typical mean diameter of 25 mm. The structure to be examined can be, for example, a hole that is drilled in the fuel-injection nozzle and that is several millimeters long.

In the case of such structures, which are systematically made in objects such as, for example, the drilled hole of a fuel-injection nozzle, the target position of the structure is likewise known right from the start. In many cases, the production of such objects is carried out with great precision, that is to say, with very small tolerances between the target position and the actual position, so that the tolerance volume is very small and the magnification factor can advantageously be selected correspondingly high.

According to a variant,

A) the object to be examined is rotated incrementally around an axis of rotation in order to create the CT image, B) for each of the rotational positions that the object to be examined thus passes through, a two-dimensional transmission X-ray image of the object to be examined is taken with the detector, and C) the three-dimensional CT image is created on the basis of the two-dimensional transmission X-ray images thus obtained.

According to another variant,

D) after steps A) and B) have been carried out, the object to be examined is shifted translatorily by a certain distance, preferably in a direction parallel to the axis of rotation, and then once again rotated incrementally around the axis of rotation;

E) for each of the rotational positions that the object to be examined passes through in step D), a two-dimensional transmission X-ray image of the object to be examined is once again taken with the detector, and F) another three-dimensional CT image is created on the basis of the two-dimensional transmission X-ray image obtained in step E).

Steps D) to F) can be repeated several times.

According to another variant of the invention, in order to create a three-dimensional CT image, the object to be examined is not only rotated incrementally around a predefinable angle of rotation, but rather, after each of these rotation increments, it is shifted translatorily by a certain distance so that the points of the object to be examined that do not lie on the rotational axis describe an essentially spiral trajectory.

In addition to the location of the structure, the shape of the structure can also be determined on the basis of the CT image or the CT data record. For example, the shape of the boundary surface of a small drilled hole in a fuel-injection nozzle can be measured very precisely by means of the invention. Here, the target position of the structure can be related to a selected point of the structure, whereby the coordinates of additional points of the structure relative to this point of the structure can be determined on the basis of the CT image. The coordinates of points of the structure determined in this way can be used, for instance, for the parameterization of the shape of the structure.

According to another variant, the shape of the structure rather than the location of the structure is determined on the basis of the CT image or the CT data record.

The relative location and the relative orientation between the MI coordinate system and the CT coordinate system can be determined in that the position of at least three, preferably at least four, selected space points of a calibration object is determined with the CT scanner in the CT coordinate system as well as with the coordinate measuring instrument in the MI coordinate system. The comparison of the results thus obtained makes it possible to determine the relative location and the relative orientation of the CT coordinate system relative to the MI coordinate system, for example, a transformation matrix for transforming these two coordinate systems into each other. If more than three space points are then calibrated in the manner described, the above-mentioned coordinate transformation is mathematically overdetermined; the redundant results, however, can advantageously be combined in order to decrease the mean error and thus to increase the precision achieved.

The object to be examined and the calibration object can, of course, be identical. By the same token, the selected points of the object to be examined can coincide with the space points used for the reciprocal calibration of the two coordinate systems.

According to a preferred variant, the CT scanner and the multisensor coordinate measuring instrument are integrated into one single device.

BRIEF DESCRIPTION OF THE SEVERAL
VIEWS OF THE DRAWING(S)

FIG. 1 schematically shows an embodiment of a device according to the invention for determining the actual position and the shape of a structure of an object to be examined 1 in a coordinate system.

DETAILED DESCRIPTION OF THE INVENTION

The device of FIG. 1 serves to determine the actual position and the shape of a structure of an object to be examined in a coordinate system. The device comprises a computed tomography scanner, hereinafter referred to as the CT scanner, with a coordinate system related thereto, hereinafter referred to as the CT coordinate system, and a multisensor coordinate measuring instrument with a coordinate system related thereto, hereinafter referred to as the MI coordinate system.

The CT scanner comprises an X-ray source 5 and a two-dimensional position-resolving detector 6. The target position of the structure is predefined relative to at least three selected, non-co-linear points of the object to be examined 1. The actual position of the structure differs from the target position by a tolerance deviation at the most, so that the actual position lies within a, for example, spherical, tolerance volume whose edge is at a distance from the target position by the tolerance deviation at the most. The relative location and the relative orientation of the CT coordinate system relative to the MI coordinate system are known or can be determined by means of calibration.

By means of the coordinate measuring instrument, the location of the at least three selected points of the object to be examined 1 can be determined relative to the MI coordinate system. The target position of the structure relative to the MI coordinate system can be calculated from this. The target position of the structure can be converted from the MI coordinate system to the CT coordinate system, so that the location thereof can be determined in the CT coordinate system.

The relative position of the object to be examined 1 relative to the CT scanner can be regulated by means of a traveling mechanism 3, using the target position of the structure relative to the CT coordinate system, in such a way that the tolerance volume and thus also the structure lie within the volume that can be detected by the CT scanner.

The CT scanner can create a three-dimensional digital CT image of the tolerance volume, including the structure, and can store it as a CT data record so that the actual position as well as the shape of the structure can be determined in the CT coordinate system on the basis of the CT data record.

The device of FIG. 1 comprises a computed tomography scanner, hereinafter referred to as a CT scanner, with an X-ray source 5 and a two-dimensional position-resolving detector, namely, a CCD matrix 6, that is sensitive to the hard X-rays, typically, for example, of 450 keV, emitted by the X-ray source 5. The device of FIG. 1 also comprises a sensor-camera unit 4 that is arranged above the object to be examined 1 and that comprises a mechanical tracer, a laser sensor as well as two cameras and that is part of a multisensor coordinate measuring instrument.

The object to be examined 1 is located on a rotation table 2 that can rotate incrementally and that is, in turn, arranged on a traveling table 3. Moreover, the rotation table 2 can be moved upwards and downwards translatorily, which is indicated by a vertical double arrow in FIG. 1.

The traveling table has a drive 9 and can be translatorily moved two-dimensionally, namely, in the plane perpendicular to the double arrow of FIG. 1. The X-ray source 5, the CCD matrix 6, the sensor-camera unit 4 as well as the traveling table 3 are arranged on a shared assembly frame 7 that rests on a base 8 that can be leveled. By moving the traveling table 3 in the direction of the X-ray source 5, the magnification factor is increased; by moving the traveling table 3 in the opposite direction, the magnification factor is decreased.

The object to be examined 1 is arranged between the X-ray source 5 and the CCD matrix 6 and, in order to create a CT image, is irradiated with the radiation from the X-ray source 5, then rotated by turning the rotation table 2, for example, by 0.9° and shifted translatorily by a certain distance by moving the traveling table 3, and then it is irradiated again, etc.

For each of the positions that the object to be examined 1 passes through, the CCD matrix 6 takes a two-dimensional transmission X-ray image of the object to be examined 1 and, from the array of two-dimensional individual images thus obtained, a three-dimensional digital image of the area of the object to be examined 1 that was detected by the CT scanner is then calculated.

This calculation is performed by a calculation and control computer 10 which, at the same time, serves to control the rotation table 2, the traveling table 3, the sensor-camera unit 4 and the X-ray source 5 and which, for this purpose, is connected via lines 13, 14, 15, 16 to the above-mentioned components. The X-ray source is supplied with electric power via a connection cable 11 and can emit an X-ray beam cone 12 that encompasses the object to be examined 1.

The CT scanner comprises the X-ray source 5, the CCD matrix 6, the calculation and control computer 10, the rotation table 2, the traveling table 3 with its drive 9, the assembly frame 7 and its base 8.

The multisensor coordinate measuring instrument comprises the sensor-camera unit 4, the calculation and control computer 10, the rotation table 2, the traveling table 3 with its drive 9, the assembly frame 7 and its base 8.

Accordingly, the calculation and control computer 10, the rotation table 2, the traveling table 3 with its drive 9, the assembly frame 7 and its base 8 are associated with the CT scanner as well as with the multisensor coordinate measuring instrument. Thus, in the device of FIG. 1, according to the invention, the CT scanner and the multisensor coordinate measuring instrument are integrated into one single device.

The commercial applicability of the invention lies in the fact that it can be used for nondestructive testing and monitoring of objects, especially mass-produced parts. The invention can likewise be used in medical technology as well as in nondestructive material testing for locating and measuring internal structures. The special usefulness of the invention is that enclosed structures in an object, for example, voids or cavities, can be located without destroying or opening the object and can be measured right away with high precision as compared to the prior art.

LIST OF THE REFERENCE NUMERALS 1 object to be examined
2 rotating table
3 traveling table
4 sensor-camera unit
5 X-ray source
6 CCD matrix
7 assembly frame
8 base
9 drive for the traveling table
10 calculation and control computer
11 connection cable of the X-ray source
12 X-ray beam cone from the X-ray source
13-16 lines

The invention claimed is:

1. Method for determining the actual position of a structure of an object (1) to be investigated in a coordinate system, wherein a computer tomograph employing CT-technology with a first coordinate system referring to the computer tomograph, a CT-coordinate system, and a coordinate measurement instrument, which coordinate measurement instrument is either a tactile or optical coordinate measurement apparatus, a multisensor coordinate measurement apparatus, or an ultrasound coordinate measurement apparatus, with a second coordinate system referring to this coordinate measurement instrument, an MI-coordinate system, are employed wherein a) the coordinates of the object (1) to be investigated are determined in the MI-coordinate system,
b) a set point position of the structure within the object (1) to be investigated is pregiven,
c) the set point position is determined in the MI-coordinate system after performing the steps a) and b),
d) and wherein the computer tomograph and the object (1) to be investigated are positioned relative to each other under employing the determination of step c) that the set point position of the structure becomes to be situated within a volume captured by the computer tomograph, or aa) the coordinates of the object (1) investigated are determined in the CT-coordinate system,
bb) a set point position of the structure is pregiven within the object (1) to be investigated,
cc) the set point position after performing the steps aa) and bb) is determined in the CT-coordinate system,
dd) and the computer tomograph and the object (1) to be investigated are positioned relative to each other under the employment of the determination of step cc) that the set point position of the structure comes to be situated within the region capturable by the coordinate measurement instrument.

2. Method according to claim 1 wherein
the computer tomograph is positioned such under employing the determination of step c) that the set point position of the structure comes to be situated within the volume captured by the computer tomograph, or
the computer tomograph such positioned according to step dd) under employing the determination of step cc) that the set point position of the structure comes to be situated within the region capturable by the coordinate measurement instrument.

3. Method according to claim 1, wherein,
while referring to at least three selected non-collinear points of the object (1) to be investigated of a pregiven set point position of the structure, the computer tomograph and the object (1) to be investigated are positioned relative to each other with the aid of the coordinate measurement instrument such that at least a part of the object (1) to be investigated is situated within the volume captured by the computer tomograph and this part of the object (1) to be investigated contains the set point position of the structure.

4. Method according to claim 1, wherein
the computer tomograph and the object (1) to be investigated are positioned relative to each other with the aid of the coordinate measurement instrument with a pregiven maximum deviation of the set point position from the actual position of the structure of the object (1) to be investigated such that both the set point position as well as also the actual position of the structure are situated in the volume captured by the computer tomograph.

5. Method according to claim 4, wherein
the actual position is different from the set point position by at most a pregiven tolerance deviation such that the actual position is situated within the tolerance volume, wherein an edge of the tolerance volume is removed from the set point position by at most the tolerance deviation, and
the computer tomograph and the object (1) to be investigated with the aid of the coordinate measurement instrument are positioned relative to each other such that the tolerance volume is completely disposed within the volume captured by the computer tomograph.

6. Method according to claim 5, wherein
the tolerance volume is a sphere, the tolerance sphere, wherein the center point of the tolerance sphere coincides with the set point position and wherein the radius of the tolerance sphere is pregiven by the amount of the maximum deviation of the set point position from the actual position of the structure.

7. Method according to claim 5, wherein
the computer tomograph or the object (1) to be investigated are positioned relative to each other with the aid of the coordinate measurement instrument such that the volume captured by the computer tomograph has at most an x-fold spacial contents of the tolerance sphere or, respectively, of the tolerance volume, wherein x is a pregivable number larger than 1.

8. Method according to claim 1, wherein
the computer tomograph and the object (1) to be investigated are positioned relative to each other with the aid of the computer tomograph in reference to at least three selected non-collinear points of the object (1) to be investigated of a pregiven set point position of the structure such that at least a part of the object (1) to be investigated is situated in the region capturable by the coordinate measurement instrument and this part of the object (1) to be investigated contains the set point position of the structure, the computer tomograph and the object (1) to be investigated are positioned relative to each other with the aid of the computer tomograph with a pregiven maximum deviation of the set point position from the actual position of the structure of the object (1) to be investigated such that both the set point position as well as also the actual position of the structure are situated within the region capturable by the coordinate measurement instrument, the actual position is different from the set point position by at most a pregiven tolerance deviation such that the actual position is disposed within the tolerance region, wherein the edge of the tolerance region is remote removed from the set point position by at most the tolerance deviation, and wherein the computer tomograph and the object (1) to be investigated are positioned relative to each other with the aid of the computer tomograph such that the tolerance region is disposed completely within the region capturable by the coordinate measurement instrument.

9. Method according to claim 3, wherein
(i) the position of at least three selected points of the object (1) to be investigated relative to the MI-coordinate system is determined with the aid of the coordinate measurement instrument,
(ii) the set point position of the structure with reference to the MI-coordinate system is calculated with the aid of the measurement determinations obtained in step (i), and
(iii) the set point position of the structure is re-calculated from the MI-coordinate system to the CT-coordinate system, such that position of the set point position in the CT-coordinate system is known in the following.

10. Method according to claim 9, wherein
the computer tomograph and the object (1) to be investigated are controlled relative to each other by way of a traveling device (3) by using a set point position of the structure with reference to the CT-coordinate system obtained according to step (iii) such that the tolerance volume and therefore also the structure are disposed in the volume captured by the computer tomograph.

11. Method according to claim 1, wherein
a three-dimensional digital CT-image of the tolerance volume inclusive the structure is generated with the aid of the computer tomograph and is stored as a CT-data set and wherein the actual position of the structure in the CT-coordinate system is determined from the CT-data set.

12. Method according to claim 8, wherein
(i) the position of at least three selected points of the object (1) to be investigated is determined relative to the CT-coordinate system with the computer tomograph,
(ii) the set point position of the structure with reference to the CT-coordinate system is calculated with the aid of the measurement determinations obtained in step (i),
(iii) the set point position of structure is re-calculated from the CT-coordinate system to the MI-coordinate system such that the position of the set point position is known in the CT-coordinate system in the following,
(iv) the object (1) to be investigated and the coordinate measurement instrument are controlled relative to each other with a traveling device (3) under employment of the set point position of the structure with reference to the MI-coordinate system obtained according to step (iii) such that the tolerance volume and therefore also the structure is disposed in the region capturable by the coordinate measurement instrument, and
(v) a three-dimensional digital image of the tolerance region inclusive of the structure is generated with the aid of the coordinate measurement instrument and is stored as a MI-data set and the actual position of the structure in the MI-coordinate system is determined from the MI-data set.

13. Method according to claim 1, wherein
such a computer tomograph is employed which has an x-ray source (5) and a two-dimensional spatially resolving detector (6), wherein the two-dimensional spatially resolving detector (6) has an active detector surface, wherein the active detector surface is sensitive to the x-ray radiation emitted by the x-ray source (5), wherein the image field of the computer tomograph is given by the size of the active detector surface, wherein the set point position of the structure is pregiven with reference to at least three selected non-collinear points of the object (1) investigated and wherein the actual position differs from the set point position by at most a tolerance deviation, such that the actual position is disposed within a sphere shaped tolerance volume, wherein the edge of the sphere shaped tolerance volume is removed from the set point position by at most the tolerance deviation, and the relative position and the relative orientation of the CT-coordinate system relative to the MI-coordinate system is known or is determined by calibration, and wherein the following steps are performed:

a) the position of at least three selected points of the object (1) to be investigated are determined relative to the MI-coordinate system with the coordinate measurement instrument b) the set point position of the structure with reference to the MI-coordinate system is calculated with the measurement determinations obtained in step a), c) the set point position of the structure is re-calculated from the MI-coordinate system to the CT-coordinate system such that the position of the set point position is known in the CT-coordinate system, d) the relative position of the object (1) to be investigated relative to the computer tomograph is controlled with a traveling device (3) by employing a set point position of the structure with reference to the CT-coordinate system and obtained according to step c) such that the tolerance volume and therefore also the structure are disposed in that volume, which volume the computer tomograph is capable of capturing, e) a three-dimensional digital CT-image of the tolerance volume inclusive the structure is generated with the aid of the computer tomograph and stored as a CT-data set, and f) the actual position of the structure in the CT-coordinate system is determined from the CT-data set.

14. Method according to claim 13,
wherein the tolerance volume is a tolerance sphere and such that the radius of the tolerance sphere is given by the tolerance deviation and the center point of the tolerance sphere is given by the set point position.

15. Method according to claim 13,
wherein the computer tomograph and the object (1) to be investigated are controlled relative to each other according to method step d) such that the center of the tolerance volume is disposed essentially in the center of the volume capturable by the computer tomograph.

16. Method according to claim 13,
wherein the computer tomograph and the object (1) to be investigated are controlled relative to each other such that the image field is completely filled by a projection of the tolerance volume onto the detector in case of a centered projection of the tolerance volume with the x-ray source (5) as a projection center.

17. Method according to claim 15,
wherein the computer tomograph and the object (1) to be investigated are controlled relative to each other such that upon a centered projection of the tolerance volume with the x-ray source (5) as a projection center:
the smallest diameter of the projection of the tolerance volume onto the detector and the smallest diameter of the image field of the computer tomograph are essentially of the same size,
the largest diameter of the projection of the tolerance volume onto the detector and the largest diameter of the image field of the computer tomograph are essentially of the same size, or
the largest diameter of the projection of the tolerance volume onto the detector and the smallest diameter of the image field of the computer tomograph are of essentially the same size.

18. Method according to claim 1,
wherein in addition to the position of the structure also the shape of the structure is determined from the CT-image or the CT-data set.

19. Method according to claim 1,
wherein the position of at least three selected on points of a calibration object are determined both with the computer tomograph in the CT-coordinating system as well as also with the coordinate measurement instrument in the MI-coordinate system and wherein the relative position and the relative orientation of the CT-coordinate system relative to the MI-coordinate system are determined by comparison of the determinations obtained in this manner.

20. Method according to claim 19,
wherein the object (1) to be investigated and the calibration object are identical.

21. Method according to claim 1, wherein
A) the object (1) to be investigated is rotated stepwise around a rotation axis for generating of the CT-image, B) a two-dimensional through radiation x-ray image of the object (1) to be investigated is taken with the detector (6) for each of the rotation positions of the object (1) to be investigated run through in this manner, and C) the three-dimentional CT- image is generated of the two-dimensional through radiation x-ray images obtained in this manner.

22. Method according to claim 21, wherein
D) the object (1) to be investigated after performing the steps A) and B) is shifted translationally by a certain distance in the direction parallel to the rotation axis and thereupon the object (1) to be investigated is again rotated stepwise around the rotation axis;

E) again a two-dimensional through radiation x-ray image of the object (1) to be investigated is taken with the detector (6) for each one of the rotation positions of the object (1) to be investigated run through according to step D); and F) a further three-dimensional CT-image is generated from the two-dimensional through radiation x-ray images obtained according to step B).

23. Device for determining the actual position of a structure of an object (1) to be investigated in a coordinate system, with a computer tomograph with the first coordinate system referring to the computer tomograph, CT-coordinate system, and a coordinate measurement instrument, which either is a tactile or optical coordinate measurement apparatus, a multisensor coordinate measurement apparatus, or an ultrasound coordinate measurement apparatus, with a second coordinate system referring to the coordinate measurement instrument, MI-coordinate system, wherein the coordinates of the object (1) to be investigated are determinable in the MI-coordinate system and wherein a set point position of the structure within the object (1) to be investigated is pregiven, such that the set point position is determinable in the MI-coordinate system, the computer tomograph and the object (1) to be investigated are positionable relative to each other with the aid of the coordinate measurement instrument with reference to at least three selected noncollinear points of the object (1) to be investigated such that at least a part of the object (1) to be investigated is situated within the volume captured by the computer tomograph and this part of the object (1) to be investigated contains the set point position of the structure, wherein the set point position of the structure comes to be situated within the volume captured by the computer tomograph, wherein the computer tomograph and the multisensor coordinate measurement instrument are integrated to a single device.

24. Device according to claim 23,
wherein the computer tomograph is positionable with the aid of the coordinate measurement instrument with reference to at least three selected noncollinear points of the object (1) to be investigated of a pregiven set point position of the structure such that at least a part of the object (1) to be investigated is situated in the volume captured by the computer tomograph and this part of the object (1) to be investigated contains the structure, wherein the set point position of the structure comes to be located within the volume captured by the computer tomograph.

25. Device according to claim 23,
the computer tomograph and the object (1) to be investigated are positionable relative to each other with the aid of the coordinate measurement instrument at a pregiven maximum deviation of the set point position from the actual position of the structure of the object (1) to be investigated such that both the set point position as well as the actual position of the structure are situated in the volume captured by the computer tomograph.

26. Device according to claim 25, wherein
the actual position differs from the set point position by at most a pregiven tolerance deviation such that the actual position is disposed within the tolerance volume, wherein the edge of the tolerance volume is removed from the set point position by at most the tolerance deviation, and
the computer tomograph and the object (1) to be investigated are positionable relative to each other with the aid of the coordinate measurement instrument such that the tolerance volume is contained completely in the volume captured by the computer tomograph.

27. Device according to claim 26,
wherein the tolerance volume is a sphere, the tolerance sphere, wherein the center point of the tolerance sphere coincides with the set point position and wherein the radius of the tolerance sphere is pregiven by the amount of the maximum deviation of the set point position from the actual position of the structure.

28. Device according to claim 26,
wherein the computer tomograph and the object (1) to be investigated are positionable relative to each other with the aid of the coordinate measurement instrument such that the volume captured by the computer tomograph has at most the x-fold spacial contents of the tolerance sphere or, respectively, of the tolerance volume, wherein x is a pregiven number larger than 1.

29. Device according to claim 23, wherein the relative position and relative orientation of the CT-coordinate system relative to the MI-coordinate system are pregiven or are determinable by a measurement.

30. Device according to claim 29, wherein
(i) the position of the at least three selected points of the object (1) to be investigated are determinable relative to the MI-coordinate system with the coordinate measurement instrument,
(ii) the set point position of the structure with reference to the MI-coordinate system is calculatable with the aid of the measurement determinations obtained according to feature (i), and
(iii) the set point position of the structure is re-calculatable from the MI-coordinate system to the CT-coordinate system such that the position of the set point position is determinable in the CT-coordinate system.

31. Device according to claim 30,
wherein the object (1) to be investigated relative to the computer tomograph and the computer tomograph are controllable relative to each other with the traveling device (3) under employment of the set point position of the structure obtained according to feature (iii) with respect to the CT-coordinate system such that the tolerance volume and therefore also the structure are disposed in the volume captured by the computer tomograph.

32. Device according to claim 23,
wherein a three-dimensional digital CT-image of the tolerance volume inclusive the structure is produceable with the aid of the computer tomograph and is storable as a CT-data set and wherein the actual position of structure in the CT-coordinate system is determinable from the CT-data set.

33. Device according to claim 23, wherein
the computer tomograph includes an x-ray source (5) and a two-dimensional spatially resolving detector (6), wherein the two-dimensional spatially resolving detector (6) has an active detector surface, wherein the active detector surface is sensitive to the x-ray radiation emitted by the x-ray source (5),
the image field of the computer tomograph is given by the size of the active detector surface,
the set point position of the structure is pregiven relative to at least three selected noncollinear points of the object (1) to be investigated and the actual position differs by at most the tolerance deviation from the set point position such that the actual position is disposed a sphere shaped tolerance volume, wherein the edge of the tolerance volume is removed by at most the tolerance deviation from the set point position, and
the relative position and the relative orientation of the CT-coordinate system relative to the MI-coordinate system are known or determinable by measurement, wherein
a) the position of the at least three selected points of the object (1) to be investigated relative to the MI-coordinate system are determinable by way of the coordinate measurement instrument,
b) the set point position of the structure relative to the MI-coordinate system is calculatable from a determination according to feature a),
c) the set point position of the structure is recalculatable from the MI-coordinate system to the CT-coordinate system such that the position of the set point position of the structure is determinable in the CT-coordinate system,
d) the relative position of the object (1) to be investigated with respect to the computer tomograph is controllable by way of a traveling device (3) under employment of the set point position of the structure with respect to the CT-coordinate system such that the tolerance volume and therefore also the structure is disposed within that volume, which volume the computer tomograph is capable of capturing, and
e) the computer tomograph is capable to generate a three-dimensional digital CT-image of the tolerance volume inclusive the structure and to store the same as a CT-data set, such that the actual position as well as the shape of the structure are determinable in the CT-coordinate system from the CT-data set.

34. Device according to claim 33,
wherein the tolerance volume is a tolerance sphere such that the radius of the tolerance sphere is given by the tolerance deviation and the center point of the tolerance sphere is given by the set point position.

35. Device according to claim 33,
wherein the computer tomograph and the object (1) to be investigated are controllable relative to each other such that center of the tolerance volume essentially is disposed in the center of the volume capturable by the computer tomograph.

36. Device according to claim 33,
wherein the computer tomograph and the object (1) to be investigated are controllable relative to each other such that the image field is filled completely by the projection of the tolerance volume onto the detector with a centered projection of the tolerance volume with the x-ray source (5) as a projection center.

37. Device according to claim 33, wherein the computer tomograph and the object (1) to be investigated are controllable relative to each other such that upon a centered projection of the tolerance volume with the x-ray source (5) as a projection center the smallest diameter of the projection of the tolerance volume onto the detector and the smallest diameter of the image field of the computer tomograph are essentially of the same size, the largest diameter of the projection of the tolerance volume onto the detector and the largest diameter of the image field of the computer tomograph are essentially of the same size, or the largest diameter of the projection of the tolerance volume onto the detector and the smallest diameter of the image field of the computer tomograph are essentially of the same size.

38. Method for determining the actual shape of a structure of an object (1) to be investigated in a coordinate system, wherein a computer tomograph employing CT-technology with a first coordinate system referring to the computer tomograph, a CT-coordinate system, and a coordinate measurement instrument, which coordinate measurement instrument is either a tactile or optical coordinate measurement apparatus, a multisensor coordinate measurement apparatus, or an ultrasound coordinate measurement apparatus, with a second coordinate system referring to this coordinate measurement instrument, an MI-coordinate system, are employed wherein a) the coordinates of the object (1) to be investigated are determined in the MI-coordinate system, b) a set point shape of the structure within the object (1) to be investigated is pregiven, c) the set point shape is determined in the MI-coordinate system after performing the steps a) and b), d) and wherein the computer tomograph and the object (1) to be investigated are positioned relative to each other under employing the determination of step c) that the set point shape of the structure becomes to be situated within a volume captured by the computer tomograph, or aa) the coordinates of the object (1) investigated are determined in the CT-coordinate system, bb) a set point shape of the structure is pregiven within the object (1) to be investigated, cc) the set point shape after performing the steps aa) and bb) is determined in the CT-coordinate system, dd) and the computer tomograph and the object (1) to be investigated are positioned relative to each other under the employment of the determination of step cc) that the set point shape of the structure comes to be situated within the region capturable by the coordinate measurement instrument.

\* \* \* \* \*